United States Patent [19]

Dockhorn

[11] 3,949,753

[45] Apr. 13, 1976

[54] APPARATUS FOR SUPPLYING ASEPTIC FLUIDS

[76] Inventor: Rolf Dockhorn, Im Rosengartle 4a, 75 Karlsruhe-Durlach, Germany

[22] Filed: Nov. 26, 1973

[21] Appl. No.: 418,962

[30] Foreign Application Priority Data
Nov. 27, 1972  Germany............................ 2258069
June 16, 1973  Germany..................... 7322503[U]

[52] U.S. Cl................ 128/303 R; 222/95; 222/209
[51] Int. Cl.²......................................... A61B 17/16
[58] Field of Search......... 222/399, 386, 94, 95, 99, 222/209; 128/303.1, 173 R, 145.8, 273, 399, 400, 401, 230, 303 R; 62/293

[56] References Cited
UNITED STATES PATENTS

| 2,440,365 | 4/1948 | Copping et al................. 222/95 UX |
| 2,505,798 | 5/1950 | Skinner........................... 222/399 X |
| 3,055,553 | 9/1962 | Mapes et al. ................... 222/399 X |
| 3,199,511 | 8/1965 | Kulick.............................. 222/95 X |
| 3,256,876 | 6/1966 | Elam............................... 128/145.8 |
| 3,256,894 | 6/1966 | Sherman......................... 222/209 X |
| 3,358,648 | 12/1967 | Berens........................... 128/303.1 |
| 3,396,724 | 8/1968 | Freytag........................... 128/145.6 |
| 3,398,738 | 8/1968 | Lamb et al...................... 128/303.1 |
| 3,411,483 | 11/1968 | Candy............................. 62/293 X |
| 3,838,794 | 10/1974 | Cogley et al..................... 222/95 |

Primary Examiner—Channing L. Pace

[57] ABSTRACT

An apparatus for supplying aseptic fluids to a field of operation, as in surgery, especially bone surgery, includes a holder for the aseptic fluid which has elastically deformable walls, an outlet pipe which can be connected to the operating field, and a container surrounding the deformable holder to which a controlled supply of pressure fluid can be furnished to regulate the supply of fluid to the point of operation.

2 Claims, 2 Drawing Figures

APPARATUS FOR SUPPLYING ASEPTIC FLUIDS

BACKGROUND OF THE INVENTION

1. Field of the Invention

The invention relates to an apparatus for supplying aseptic fluid to a field of operation, in which grinding, polishing and/or dupping is carried out, as by drills, cutters, saws and the like, especially for bone surgery.

2. The Prior Art

In grinding, polishing and especially in boring operations on bones there arises an undesirable heating of the tool and the bone as well as the drying of the bone chips in the area of the operation. In order to lead off the heat resulting from a rapid boring operation from the field of operation and to cool the tool as well as to prevent a drying out of the chips, the supplying of fluid cooling medium is desirable.

In dental practice, it is known, for example during drilling, to supply fluid in the form of a water spray to the point of filling for the cooling and washing away of the chips. The medium supplied as well as the equipment for supplying it are not sterile. In this respect, the known arrangements are not suitable for the supply of fluid to the operation field which must be kept sterile. In surgical practice at times the aseptic fluid is supplied with hand sprays to the working field. It is obvious that in this manner there is danger of a local overheating of the bone as well as of the tool and the danger of a drying of the bone chip which can only be overcome very insufficiently.

SUMMARY OF THE INVENTION

With consideration of this difficulty the present invention supplies an apparatus with which the supply of cooling medium in the form of an aseptic fluid to the field of operation or work field is possible and an adequate cooling of the tool and the bone at the point of operation is assured and the danger of a drying of the bone chips is effectively avoided.

In solving this problem, the apparatus according to the invention is characterised by a holder for holding the aseptic fluid provided with elastically deformable walls to which a movable conducting pipe leading to the field of operation is connected, from which aseptic fluid can be driven by this pipe through a fluid operating on the walls of the container from the outside, so that a control of the quantity of outflow can be accomplished through control of the pressure exerted on the holder.

In an especially advantageous modification of the invention, the apparatus is characterised in that the holder which contains the aseptic fluid is enclosed in a container which can be influenced from the outside with pressure medium, for instance air pressure, and in this way is itself subjected to an outer supply of pressure medium. This arrangement then contemplates a holder and a container, one within the other, which in a controllable manner are supplied with pressure medium, so that the inner container or holder which holds the aspetic fluid lies under the influence of the pressure medium. Thus aseptic fluid is pressed out of the holder through an outlet pipe connected with the holder.

In a further modification the invention can provide a control means for the supply of the pressure medium and thus of the pressure on the holder which holds the aseptic fluid.

According to additionally important characteristics, the movable outlet passage leading to the working or operation field can be provided with an adjustable throttle valve for the control of the quantity of fluid passing through the passage per unit of time and/or with a sterilizable check valve which permits a flow of fluid only in the direction of the field of operation. Through this arrangement such a check valve is provided to prevent during interruption of the operation any backflow of fluid remaining in the outlet pipe.

BRIEF DESCRIPTION OF THE DRAWINGS

Further characteristics, advantages and details of the invention will be clear from the foregoing drawings, in which.

DESCRIPTION OF THE PREFERRED EMBODIMENTS

Figure 1:
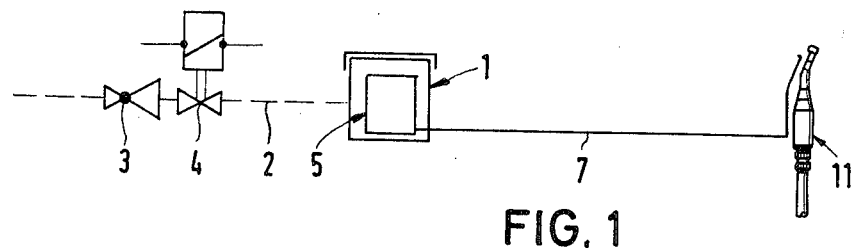
FIG. 1 shows in schemmatic view in its totality with a means for control of the pressure on the holder which holds the aseptic fluid.
Figure 2:
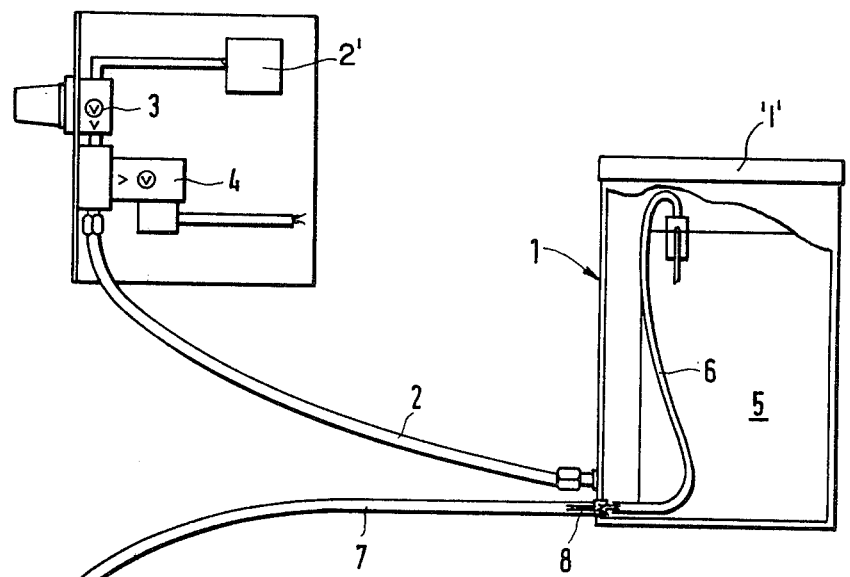
FIG. 2 is a view on a larger scale than FIG. 1 of the apparatus according to the invention for the supply of aseptic fluid to the field of operation.
Figure 2:
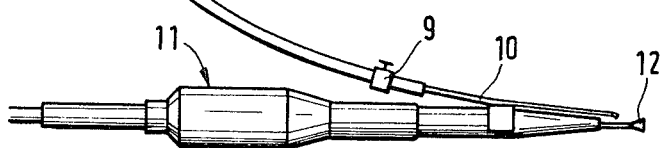

The apparatus is especially useful for drilling in bone surgery. The supply of aseptic fluid to the working field is desired in order to prevent the heating of the tool and of the bone as well as the drying of the bone chips.

The form of the invention disclosed consists of an outer receiving container 1 provided with a removable cover 1'. Connected to this container is a connecting tube 2, by which the interior of the container can be supplied with a pressure medium, such as air or water under pressure. The pressure medium for supplying the pressure 1 is supplied from a source of pressure 2', for example a compressor. The supply of pressure medium to the container takes place through a control arrangement connected in the connecting pipe 2, which includes a supply valve 3 and a control valve 4 which are operable by means of a hand or foot switch, not shown. In this way the supply of pressure medium to the interior of the container can be regulated with respect to the quantity and the pressure.

The foregoing outer container 1 contains a holder 5 filled with an aseptic fluid, which is interchangeably arranged in the outer container. As the holder for the aseptic fluid, especially for medicinal purposes, available holders of plastic material are suitable comprising infusion flasks with a physiological salt solution. An outlet pipe for the aseptic fluid is connected to the holder 5, which is composed of two pipes 6 and 7, and a pipe connection 8 which is fluid-tightly but interchangeably arranged in the wall of the outer container 1, in which there may be provided a check valve, which permits flow only towards the field of operation. The interchangeability of the pipe connection 8 is necessary because it must be possible to sterilize every part of the outlet pipe. Pipes used in medicine for infusion are especially suitable for the outlet connection. The end of the pipe 7 remote from the outer container 1 is provided with a regulating adjustable throttle valve 9 and with a metal pipe 10 with a hand piece 11 which is connected to the boring, grinding or cutting tool. This metal pipe 10, which is sterilized like the other parts of the outlet pipe reaches into the immediate neighborhood of the hand or angle piece 11 which carries the tool 12.

The sterile fluid flowing out of the fluid holder 5 passes directly to the field of operation and assures the wetting as well as the cooling of the work tool.

By the supply of the inner space of the container 1 with the pressure medium the sterile fluid contained in the holder 5 is subjected to an outer pressure. During the time of this pressure sterile fluid is forced through the outlet pipe from the inner holder 5, so that the quantity of flow and pressure of the escaping aseptic fluid are determined by the supply of pressure which produces a pressure operation on the holder 5.

In order during a short interruption of the operation to be able to break off any further supply of aseptic fluid to the field of operation for a short time, the construction of the control 3, 4 for the supply of pressure medium is advantageously such that through the corresponding operation of the control means a flow off of the pressure medium from the inside of the outer container 1 takes place and no backflow, or at least a very limited one, takes place of the quantity of fluid in the outlet pipe to the holder 5 for the aseptic fluid.

The prevention of the backflow of fluid in the outlet pipe is also from this stand point of significance in that there can be a movement of fluid to the outlet opening of the metal pipe 10. It is obvious that this possibly unsterile fluid during an interruption of the operation should not be let back into the arrangement which holds the aseptic fluid.

If instead of the measures set forth above or in addition thereto, generally in the outlet stud 8, which is fixed in the wall of the outer container 1, a check valve is provided, which also must be sterilized and which permits flow only in the direction towards the field of operation, so that any backflow of the fluid in the outlet pipe is prevented.

Upon complete exhaustion of the aseptic fluid fed from the holder 5, in a simple way the exchange of the empty holder for a full holder can be accomplished, whereupon a new operation of the apparatus takes place.

The valve 3 thus allows the flow of pressure fluid to the inside of container 1. The valve 4 is an arrangement for opening the inner space of the container 1, so that pressure medium can escape therefrom.

If the inner space of the container 1 is provided with pressure medium through the valve 3 in the pipe 2, aseptic fluid is pressed from the holder 5 by the pressure working out on the outside thereof in accordance with the supply of such pressure medium. In general there is a constant flow of aseptic fluid, and a constant supply of pressure medium. If the progress of the operation is interrupted, and the supply of aseptic fluid must be cut off, the supply of pressure medium to the container 5 must be stopped. This occurs if the valve 4 is open, on which occasion there is no further supply of pressure medium to the space within the container 1 and the pressure medium flows off through the valve 4.

The flow of aseptic fluid, which is furnished by the supply of pressure medium to the container 1 at a substantially constant rate, is dependent on the cross-section of the flow, which can be changed by the throttle valve 9, so that at the point of operation the quantity of fluid supplied per unit of time can be varied.

I claim:

1. Apparatus for feeding aseptic fluids to a field of operation comprising a holder for aseptic fluids having elastically deformable walls, an outlet pipe connected to said holder for directing fluid to a field of operation, and means for applying pressure on the outside of such walls, said pressure applying means being adjustable to control the quantity of outflow from the holder, the means for applying pressure including a closed container enclosing the holder and means for supplying a compressible fluid under pressure to said container on the outside of the holder, means for controlling the supply of pressure medium to the container, said outlet pipe including an adjustable throttle valve for controlling the quantity of fluid flowing therethrough per unit of time, the outlet pipe containing a check valve means for permitting flow only in the direction away from the holder and preventing back flow in the outlet pipe, the holder being interchangeably arranged in the container.

2. Apparatus as claimed in claim 1, in which the check valve is mounted in the wall of the container.

* * * * *